(12) United States Patent
Wheeler et al.

(10) Patent No.: US 11,324,955 B2
(45) Date of Patent: May 10, 2022

(54) IMPLANTABLE HUB AND SATELLITE SYSTEM FOR NEURAL RECORDING AND STIMULATION

(71) Applicant: The Charles Stark Draper Laboratory, Inc., Cambridge, MA (US)

(72) Inventors: Jesse J. Wheeler, East Boston, MA (US); Philip D. Parks, Jamaica Plain, MA (US); James E. Moran, Methuen, MA (US); Andrew Czarnecki, Cambridge, MA (US); Keith B. Baldwin, Braintree, MA (US); David Goldberg, Cambridge, MA (US); Alex Kindle, Cambridge, MA (US); Marc W. McConley, Andover, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 202 days.

(21) Appl. No.: 16/431,428

(22) Filed: Jun. 4, 2019

(65) Prior Publication Data

US 2019/0388691 A1 Dec. 26, 2019

Related U.S. Application Data

(63) Continuation of application No. 15/154,487, filed on May 13, 2016, now abandoned.
(Continued)

(51) Int. Cl.
*A61N 1/372* (2006.01)
*A61N 1/36* (2006.01)
(Continued)

(52) U.S. Cl.
CPC .......... *A61N 1/36139* (2013.01); *A61B 5/377* (2021.01); *A61B 5/4836* (2013.01);
(Continued)

(58) Field of Classification Search
CPC ............ A61N 1/36139; A61N 1/36125; A61N 1/37276; A61N 1/0534; A61N 1/36064;
(Continued)

(56) References Cited

U.S. PATENT DOCUMENTS

| 7,113,829 B2 * | 9/2006 | Lindberg | ........... A61N 1/37252 |
| | | | 607/60 |
| 8,140,160 B2 * | 3/2012 | Pless | .................... A61B 5/0031 |
| | | | 607/31 |

(Continued)

FOREIGN PATENT DOCUMENTS

| WO | 2012103519 A2 | 8/2012 |
| WO | 2012126003 A1 | 9/2012 |

OTHER PUBLICATIONS

Ghovanloo, Maysam, et al. "A Modular 32-Site Wireless Neural Stimulation Microsystem" IEEE Journal of Solid-State Circuits, vol. 39, No. 12, pp. 2457-2466, Dec. 2004.
(Continued)

*Primary Examiner* — Eugene T Wu
(74) *Attorney, Agent, or Firm* — McDermott Will & Emery LLP (57) ABSTRACT

The systems and methods described herein include an external base station with a tethered transceiver, an implanted hub that includes power, telemetry, and processing electronics, and a plurality of implanted satellite that contain reconfigurable front-end electronics for interfacing with electrodes. The system can operate in different modes. In a first mode, called a base boost mode, the external base station is used for closed-loop control of stimulation therapies. In a second, autonomous mode, closed-loop control is performed in the hub without direct influence from the base station. In a third mode, streams of neural data are transmitted to an offline processor for offline analysis.

18 Claims, 4 Drawing Sheets

Related U.S. Application Data (60) Provisional application No. 62/162,495, filed on May 15, 2015.

(51) Int. Cl.
  *H04B 1/3827* (2015.01)
  *H04L 41/0806* (2022.01)
  *H04L 43/16* (2022.01)
  *A61B 5/00* (2006.01)
  *A61N 1/05* (2006.01)
  *H04W 4/80* (2018.01)
  *A61B 5/377* (2021.01)

(52) U.S. Cl.
  CPC ....... *A61N 1/0534* (2013.01); *A61N 1/36064* (2013.01); *A61N 1/36082* (2013.01); *A61N 1/36125* (2013.01); *A61N 1/37217* (2013.01); *A61N 1/37276* (2013.01); *H04B 1/385* (2013.01); *H04L 41/0806* (2013.01); *H04L 43/16* (2013.01); *H04W 4/80* (2018.02)

(58) Field of Classification Search
  CPC ............ A61N 1/36082; A61N 1/37217; A61B 5/377; A61B 5/4836; H04W 4/80; H04B 1/385; H04L 41/0806; H04L 43/16
  See application file for complete search history.

(56) References Cited

U.S. PATENT DOCUMENTS

| | | | |
|---|---|---|---|
| 8,560,041 B2 | 10/2013 | Flaherty et al. | |
| 2003/0114897 A1* | 6/2003 | Von Arx | A61N 1/37276 607/60 |
| 2003/0144711 A1* | 7/2003 | Pless | A61B 5/0006 607/60 |
| 2005/0222631 A1* | 10/2005 | Dalal | A61N 1/37254 607/27 |
| 2006/0293578 A1* | 12/2006 | Rennaker, II | A61B 5/24 600/378 |
| 2007/0067003 A1* | 3/2007 | Sanchez | A61N 1/36082 607/45 |
| 2007/0250133 A1 | 10/2007 | Carlson et al. | |
| 2010/0228314 A1* | 9/2010 | Goetz | A61M 5/1723 607/41 |
| 2013/0012802 A1 | 1/2013 | Horseman | |
| 2014/0094674 A1* | 4/2014 | Nurmikko | A61N 1/37223 600/378 |

OTHER PUBLICATIONS

International Search Report and Written Opinion dated Aug. 1, 2016 in PCT Application No. PCT/US2016/032457.

Liu et al., "Stability of the Interface Between Neural Tissue and Chronically Implanted Intracortical Microelectrodes", IEEE Transactions on Rehabilitation Engineering, vol. 7, No. 3, Sep. 1999, pp. 315-326.

Mendez et al., "A Custom Signal Processor Based Neuroprosthesis Intended to Recover Urinary Bladder Functions", 2014 IEEE International Symposium on Circuits and Systems (ISCAS), Jun. 2014, pp. 1608-1611.

Noorsal et al., "A Neural Stimulator Frontend With High-Voltage Compliance and Programmable Pulse Shape for Epiretinal Implants", IEEE Journal of Solid-State Circuits, vol. 47, No. 1, Jan. 2012, pp. 244-256.

Nurmikko et al., "Listening to Brain Microcircuits for Interfacing With External World-Progress in Wireless Implantable Microelectronic Neuroengineering Devices", Proceedings of the IEEE, vol. 98, No. 3, Mar. 2010, pp. 375-388.

Sawan et al., "Wireless Smart Implants Dedicated to Multichannel Monitoring and Microstimulation", IEEE Circuits and Systems Magazine, First Quarter 2005, pp. 21-39.

Stieglitz et al., "Implantable Biomedical Microsystems for Neural Prostheses", IEEE Engineering in Medicine and Biology Magazine, Sep./Oct. 2005, pp. 58-65.

Office Action dated Aug. 10, 2017 in U.S. Appl. No. 15/154,487.
Office Action dated Jun. 5, 2018 in U.S. Appl. No. 15/154,487.

\* cited by examiner

IMPLANTABLE HUB AND SATELLITE SYSTEM FOR NEURAL RECORDING AND STIMULATION

CROSS-REFERENCE TO RELATED APPLICATIONS

The present application is a continuation of, and claims priority to and the benefit of, U.S. patent application Ser. No. 15/154,487, filed May 13, 2016, which claims priority to, and the benefit of, U.S. Provisional Patent Application No. 62/162,495 filed on May 15, 2015, both of which are herein incorporated by reference in their entirety.

GOVERNMENT LICENSE RIGHTS

This invention was made with government support under Contract Number W911NF-14-2-0045, Project No. 32077, awarded by the Defense Advanced Research Project Agency (DARPA). The government has certain rights in the invention.

BACKGROUND

Neuroneuropsychiatric disorders can be monitored by measuring the electrical activity of the brain. The electrical activity can be measured externally with electrodes placed on the scalp of the patient or internally with electrocorticography (ECoG) or depth electrodes. In some of these patients, deep brain stimulators are implanted to provide therapeutic electrical stimulation to target areas or structures in the brain.

SUMMARY OF THE DISCLOSURE

According to one aspect of the disclosure, a neural stimulation and recording system includes a base station. The base station includes a first low bandwidth transceiver and a high bandwidth receiver. The system also includes an implantable neural stimulation and recording hub. The hub includes a second low bandwidth transceiver that is configured to wirelessly communicate with the first low bandwidth transceiver of the base station. The hub also includes a high bandwidth transmitter that is configured to wirelessly transmit data to the high bandwidth receiver of the base station. The hub also includes a processor. The processor is configured to receive, from the base station via the second low bandwidth transceiver, a configuration setting that includes template parameters. The processor is also configured to transmit a first neural signal to the base station. The processor is also configured to receive, from the base station via the second low bandwidth transceiver, a second configuration setting. The second configuration setting includes updated template parameters that were generated in response to the first neural signal. The processor is also configured to detect a threshold crossing of a second neural signal, and determine a neuropsychiatric state responsive to the threshold crossing of the neural signal and the updated template parameters. The processor is also configured to generate an output stimulation command responsive to the determined neuropsychiatric state.

In some implementations, the first and second low bandwidth transceivers have a bandwidth between about 1 Mbps and about 5 Mbps and the high bandwidth transmitter has a bandwidth between about 5 Mbps and about 50 Mbps. In some implementations, the first and second low bandwidth transceivers are low-energy Bluetooth® transceivers.

In some implementations, the processor is configured to transmit the neural signal, via the high bandwidth transmitter, to the high bandwidth receiver of the base station. The system can also include an offline processor that is coupled to the base station. The offline processor generates the configuration setting responsive to an initial neural signal that is transmitted from the implantable neural stimulation and recording hub.

In some implementations, the system includes a plurality of satellites that are coupled to the implantable neural stimulation and recording hub. Each of the plurality of satellites include at least one electrode configured to measure the first and second neural signals. The plurality of satellites is configured to deliver an electrical stimulus responsive to the output stimulation command. In some implementations, the neuropsychiatric state is one of impulsivity, approach, avoidance, inhibition, and fear.

According to another aspect of the disclosure, a method includes receiving, at an implantable neural stimulation and recording hub, a configuration setting that includes template parameters. The configuration setting is received from a base station via a low bandwidth transceiver. The method also includes transmitting, from the implantable neural stimulation and recording hub, a first neural signal. The first neural signal is transmitted to the base station. The method also includes receiving, at the implantable neural stimulation and recording hub, a second configuration setting. The second configuration setting includes updated template parameters that were generated responsive to the first neural signal. The second configuration setting is received from the base station via the second low bandwidth transceiver. The method also includes detecting a threshold crossing of a second neural signal. The method also includes determining a neuropsychiatric state responsive to the threshold crossings of the neural signal and the updated template parameters. The method also includes generating an output stimulation command responsive to the determined neuropsychiatric state.

In some implementations, the method also includes transmitting the neural signal via a high bandwidth transmitter to a high bandwidth receiver of the base station. The low bandwidth transceiver has a bandwidth between about 1 Mbps and about 5 Mbps and the high bandwidth transmitter has a bandwidth between about 5 Mbps and about 50 Mbps. The low bandwidth transceiver is a low-energy Bluetooth® transceiver.

In some implementations, the method includes transmitting an initial neural recording to an offline processor that is coupled to the base station. The method can also include generating, by the offline processor, the configuration setting responsive to the initial neural signal.

In some implementations, the method includes detecting the first neural signal by at least one of a plurality of satellites that are coupled to the implantable neural stimulation and recording hub. The method can also include extracting a plurality of features from the second neural signal and determining the neuropsychiatric state responsive to the plurality of features.

In some implementations, the method includes delivering, by the at least one of the plurality of satellites, an electrical stimulus responsive to the output stimulation command. In some implementations, the neuropsychiatric state is one of impulsivity, approach, avoidance, inhibition, and fear.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The systems and methods described herein include an external base station with a tethered transceiver, an implanted hub that includes power, telemetry, and processing electronics, and a plurality of implanted satellites that contain reconfigurable front-end electronics for interfacing with electrodes. The systems described herein include a flexible, adaptable, and reprogrammable architecture that enables the advancement of closed-loop neural control while meeting the challenges of system power constraints. As an overview, the processing architecture of the system distributes functionality across several parts of the system. A first part, the implanted hub, handles processes that are required to run at a high update rate with low latency. To save power, these processes run with largely fixed parameter sets. A second part, the base station, includes additional processing power. In this way, the design can reduce power utilization while maintaining core capability in the constrained autonomous configuration.

The software is designed to provide flexibility to adapt the real-time processing via parameter loads to the hub. This allows the parameters and algorithms to be tailored to individual researcher and patient needs and to evolve as plasticity effects are observed from data collected from the system. Also, the flexible interface accommodates a wide variety of ways in which the system can be used at any given time, ranging from highly efficient low-power processing for autonomous operation to large-volume data collection for neuropsychiatric feature identification.

Algorithm innovations include real-time signal processing, autonomous spike sorting, neuropsychiatric state decoding, and closed-loop control algorithms optimized for low-power autonomous operation while providing the capability for adaptation and learning when data and computing resources are available.

The system can operate in different modes. In a first mode, called a base boost mode, the external base station is used for closed-loop control of stimulation therapies. High bandwidth telemetry between the hub and the base station streams neural data out of the hub to the base station for processing. Stimulation controls are returned to the hub via a lower-bandwidth, but longer range data link. In a second, autonomous mode, closed-loop control is performed in the hub without direct influence from the base station. In a third mode, streams of neural data are transmitted to an offline processor for offline analysis. Through the offline analysis the system develops custom control parameters for use by the hub and satellites. Following customization, an updated autonomous mode is used to provide continuous real-time therapy without the need for external intervention.

Figure 1:
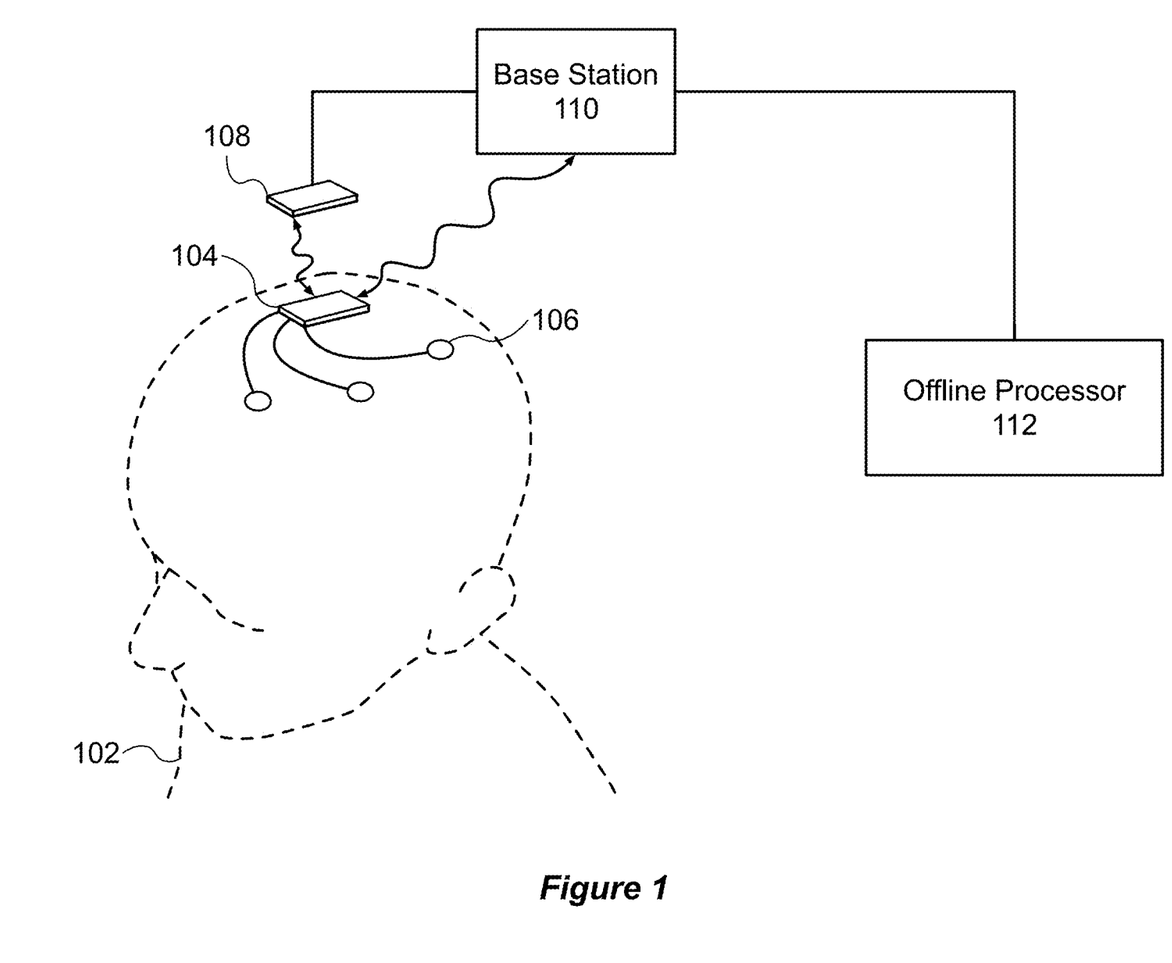
FIG. 1 illustrates a system for stimulating and recording electrical signals from a patient.

FIG. 1 illustrates a system for stimulating and recording electrical signals from a patient 102. The system 100 includes an implantable neural stimulation and recording hub 104 (also referred to as a hub 104) that is implanted below the scalp of the patient 102. Three satellites 106 are coupled to the hub 104. The satellites 106 are configured to stimulate the patient 102 and also record neural signals from the brain of the patient 102. The hub 104 communicates wirelessly to the head mounted interface 108 using a first transceiver. The head mounted interface 108 is located external to the patient 102. The head mounted interface 108 is electrically coupled to a base station 110, which is electrically coupled to an offline processor 112. The hub 104 also communicates with the base station 110 wirelessly using a second transceiver.

Figure 2:
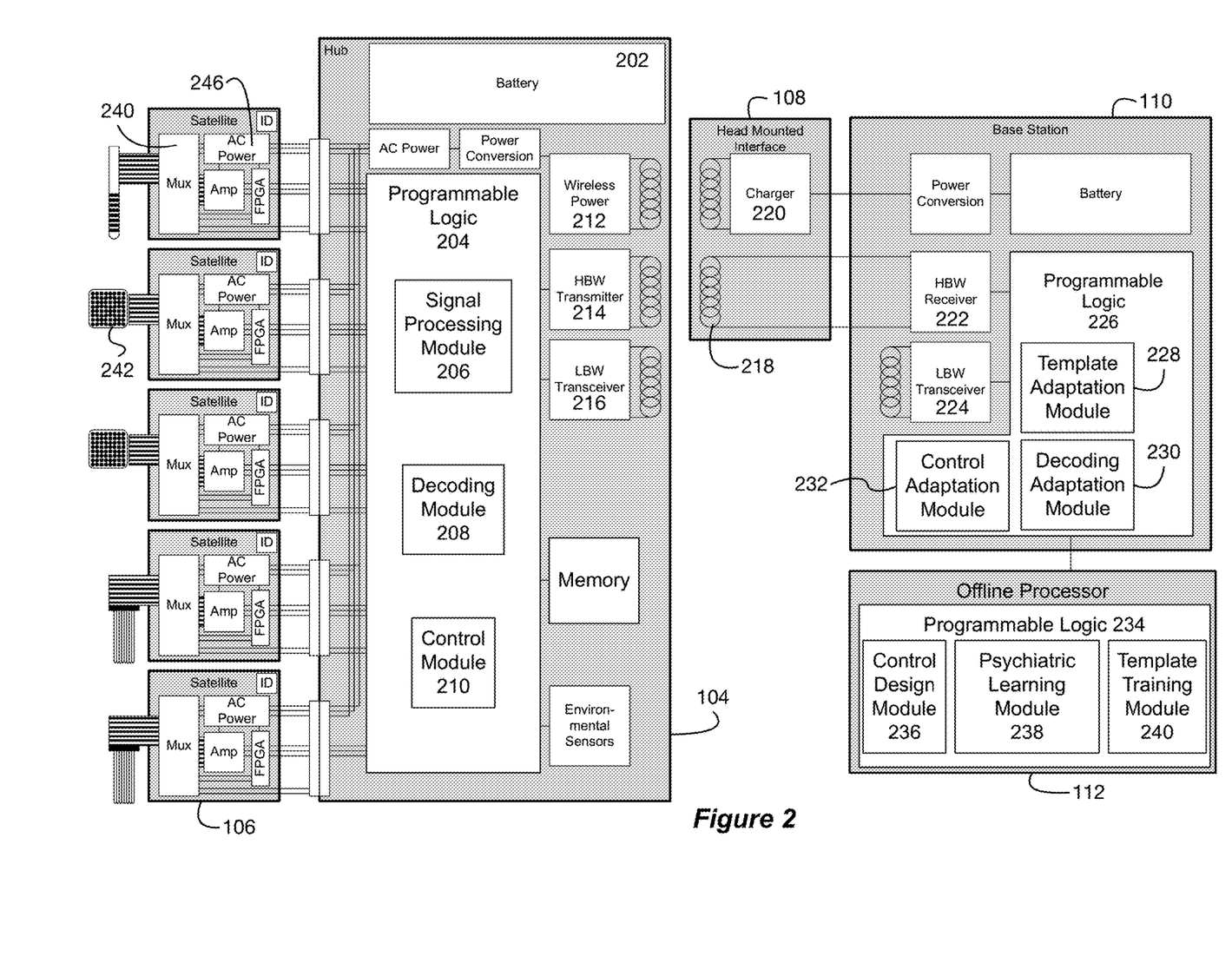
FIG. 2 illustrates a schematic of the system illustrated in FIG. 1.
Figure 3:
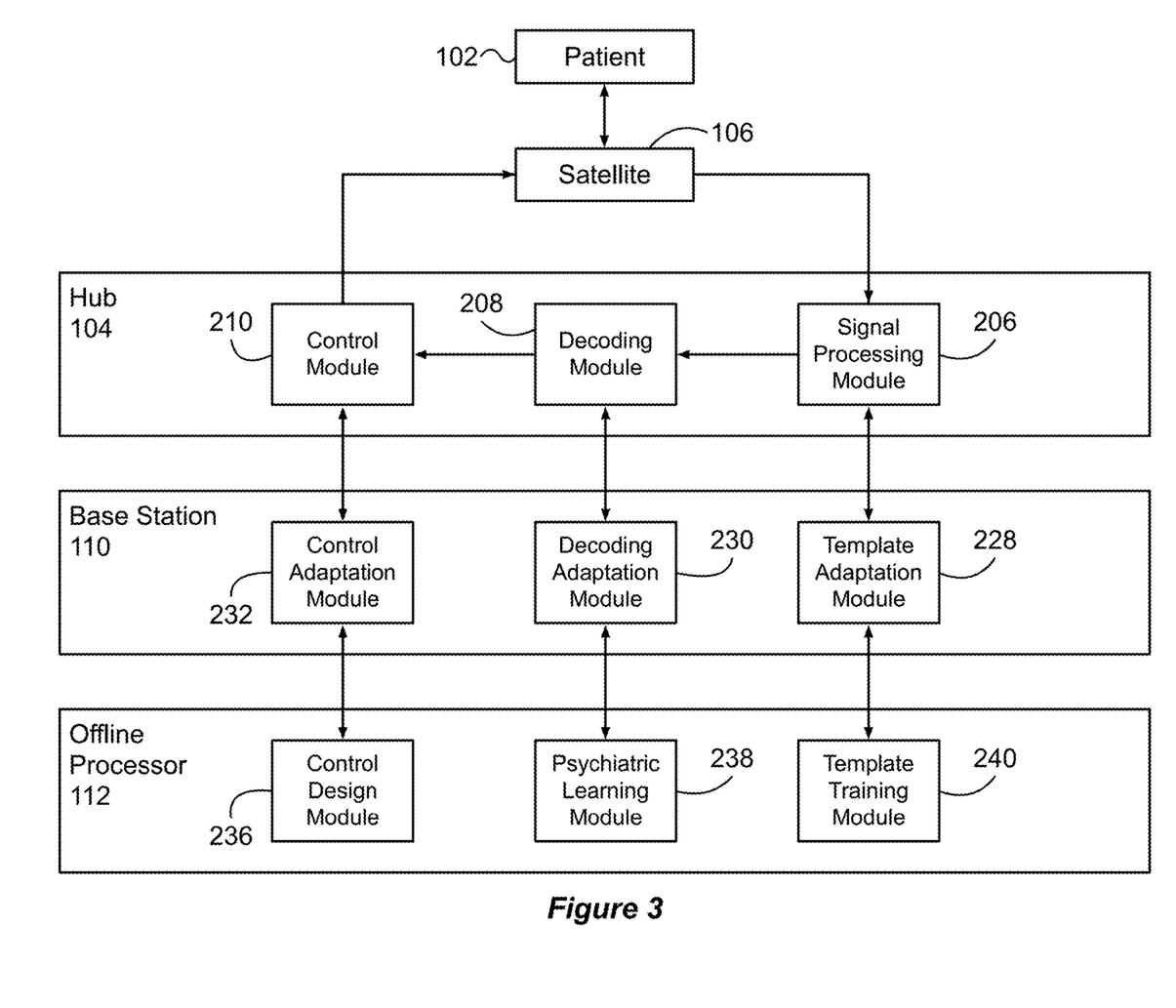
FIG. 3 illustrates a simplified schematic of the system illustrated in FIG. 1 that demonstrates the flow of data through the system.

Each of the components of the system 100 are described further in relation to FIGS. 2 and 3. As an overview of the system, and still referring to FIG. 1, the hub 104 is an implantable system that forms a distributed architecture with the satellites 106. The hub 104 coordinates the satellites' recording of electrical signals and electrical stimulation of the patient 102. The hub 104 also communicates wirelessly with the head mounted interface 108 and the base station 110 to transfer recorded electrical signals and to receive updated control models and configuration settings. The hub 104 includes multiple transceivers enabling both high and low bandwidth communication with the base station 110 and the offline processor 112. The hub 104 includes a battery that is wirelessly charged via the base station 110. The implantation of the hub 104 into the head of the patient 102 is for illustrative purposes only. The hub 104 can be implanted into other areas of the patient 102. For example, the hub 104 can be implanted in the chest of the patient 102 to stimulate and record from the heart or in the lower back to stimulate and record from the spinal column.

The system 100 also includes a plurality of satellites 106. As illustrated, the system 100 includes three satellites 106. In some implementations, the includes between about 1 and about 100, between about 1 and about 50, between about 1 and about 25, or between about 1 and about 10 satellites 106. Each of the satellites 106 can be dynamically reconfigurable stimulation and recording platforms. For example, each satellite 106 can include a plurality of channels that are dynamically reconfigurable between recording and stimulation channels. The satellites 106 include a connecter that enables different types of electrodes to be coupled to the satellites 106 during the implantation of the satellites 106 and hub 104. The different electrodes can include deep brain style depth electrodes, Michigan and Utah style electrode arrays, tetrodes, cuff electrodes, ECoG electrodes, ECoG arrays, or any combination thereof. The satellite 106 includes an interface to the hub 104 for the transmission of recorded data, stimulation signals, and configuration data. The satellites 106 receive power through their connection with the hub 104. In some implementations, the satellites 106 generate the electrical stimulus delivered to the patient 102. In other implementations, the electrical stimulus is generated by the hub 104 and transferred to the satellite 106 through a multiplexor application-specific integrated circuit (ASIC) acting as a crosspoint switch. The satellite 106 is encapsulated in a hermetically sealed implantable housing.

The head mounted interface 108 of the system 100 is configured to wirelessly communicate with the implanted hub 104. The head mounted interface 108 can wirelessly supply power to the hub 104 through induction when the head mounted interface 108 is placed in close proximity to the hub 104. The head mounted interface 108 also includes a high bandwidth receiver configured to receive high bandwidth communications from the hub 104. In some implementations, the high bandwidth communications are transmitted from the hub 104 to the head mounted interface 108 when the head mounted interface 108 is in close proximity to the hub 104.

The head mounted interface 108 is electrically coupled to the base station 110 by, for example, a high bandwidth connection such as a universal serial bus (USB) connection. The base station 110 includes one or more processors. In some configurations, the hub 104 streams data to the base station 110 in real time and the base station 110 analyzes the data in real time to perform closed loop stimulation. The base station 110 can transmit a portion or all of the streamed data to the offline processor 112 for offline processing. In some implementations, the offline processor 112 is a laptop computer, desktop computer, or other computing device.

FIG. 2 illustrates a schematic of the system 100 illustrated in FIG. 1. The hub 104 includes a battery 202 to power the hub 104 and satellites 106. The hub 104 includes programmable logic 204, which includes a signal processing module 206, a decoding module 208, and a control module 210. The hub 104 also includes a plurality of communication systems, including a wireless power antenna 212, a high bandwidth (HBW) transmitter 214, and a low bandwidth (LBW) transceiver 216.

The head mounted interface 108 includes an antenna 218 for the base station's HBW receiver 222. The head mounted interface 108 also includes the charging system 220 that inductively couples with the wireless power antenna 212 to wirelessly provide power to the battery 202 of the hub 104.

The base station 110 includes the HBW receiver 222 and a LBW transceiver 224. The base station 110 also includes programmable logic 226 that includes a template adaptation module 228, a decoding adaptation module 230, and a control adaptation module 232. The offline processor 112 includes programmable logic 234 that includes a control design module 236, a neuropsychiatric learning module 238, and a template training module 240. The distributed architecture and interaction between the modules of the programmable logic 204, 226, and 234 is described in greater detail in relation to FIG. 3.

Still referring to FIG. 2, and in greater detail, the electrical components of the hub 104 are coupled to separate circuit boards. For example, the hub 104 can include a main board that includes the programmable logic 204 and memory, a second board that includes alternating current (AC) to direct current (DC) conversion systems, and a third board that includes the wireless power antenna 212, the HBW transmitter 214, and the LBW transceiver 216 for communication with the head mounted interface 108 and base station 110. The components are then hermetically sealed in the housing of the hub 104. The separate circuit boards are coupled together with thin-film flex cables and then over-molded with medical grade silicone. In some implementations, the housing of the hub 104 includes a titanium and/or ceramic packaging. The packaging of the hub 104 (e.g., the exterior dimensions of the hub 104) is between about 50 mm and about 75 mm long, between about 25 mm and about 45 mm wide, or between about about 5 mm and about 20 mm thick.

The wireless power antenna 212 of the hub 104 inductively couples with the coils of the charging system 220 to provide power to the battery 202. In some implementations, the battery 202 is a lithium-ion rechargeable battery. The battery 202 has a charged lifetime of between about 250 mA-hrs to about 500 mA-hrs. The wireless power antenna 212 can couple with the coils of the charging system 220 at a distance of about 1 cm to about 10 cm at a frequency of about 130 kHz.

The hub 104 also includes a HBW transmitter 214. The HBW transmitter 214 is configured to provide a high data rate over a short distance without consuming significant power. In some implementations, the HBW transmitter 214 utilizes a backscatter modulation technique whereby the base station 110 generates a carrier wave that is transmitted to the hub 104. The HBW transmitter 214 modulates the reflection coefficient presented to its antenna, which generates a reflected (or "backscatter") signal. The backscattered signal contains a phase modulated data signal. In some implementations, the HBW transmission is one directional—for example, the HBW transmitter 214 of the hub 104 does not include a HBW receiver. In these implementations, control messages from the HBW transmitter 214 are multiplexed over the LBW transceiver 216. In other implementations, the HBW transmitter 214 is a HBW transceiver, which enables bi-directional HBW communication between the hub 104 and the base station 110. In some implementations, the HBW transmitter 214 operates at about 430 MHz. In some implementations, the data rate of the HBW transmitter 214 is between about 5 Mbps and about 50 Mbps, between about 5 Mbps and about 25 Mbps, or between about 15 Mbps and about 20 Mbps. The HBW transmitter 214 can have a relatively short transmission range compared to the LBW transceiver 216. For example, the HBW transmitter 214 can have a transmission range between about 10 mm and about 100 mm, between about 20 mm and about 75 mm, or between about 20 mm and about 50 mm. In some implementations, the hub 104 and the head mounted interface 108 can include magnets so the head mounted interface 108 can be magnetically coupled to the exterior of the patient 102. The magnetic coupling keeps the antenna 218 aligned with the HBW transmitter 214.

The hub 104 also includes a LBW transceiver 216. The LBW transceiver 216 is configured to have a greater range compared to the HBW transmitter 214. For example, the LBW transceiver 216 can have a transmission range of between about 1 meter and about 15 meters, between about 1 meter and about 10 meters, or between about 1 meter and about 5 meters. In some implementations, the hub 104 transmits and receives low bandwidth data to and from the base station 110 and the offline processor 112 via the LBW transceiver 216. The low bandwidth data can include hub 104 and satellite 106 health information, firmware and software updates, and direct control signals for directly controlling the satellites 106 and the hub 104 from the base station 110 or offline processor 112. The LBW transceiver 216 can have a data rate between about 1 Mbps and about 5 Mbps or between about 1 Mbps and about 3 Mbps. In some implementations, the HBW transmitter 214 is a 2.4 GHz RF modem chip. In some implementations, the LBW transceiver 216 and LBW transceiver 224 are low-energy Bluetooth® transceivers.

In some implementations, the LBW transceiver 216 operates in a master-slave mode with the LBW transceiver 224. In a master-slave mode, the primary transmitter initiates a transaction by sending a data packet to the primary receiver, and the primary receiver can respond with an acknowledgment packet or a data packet with a payload. In some implementations, the LBW transceiver 216 is the primary transmitter. This configuration can save power because the LBW transceiver 216 can remain in a sleep mode to save battery power until the LBW transceiver 216 needs to wake to transmit data. The LBW transceiver 224, which is powered by AC power, can remain active and listening for incoming data packets without concern for battery usage.

FIG. 2 also illustrates five satellites 106 coupled to the hub 104. Each satellite 106 interfaces with an electrode 242. The satellites 106 include a multiplexer 244. The multiplexer 244 acts as a crosspoint switch and enables each channel of the satellite 106 to act as a recording or a simulation channel. The satellite 106 is powered using AC power from the hub 104. The AC power converter 246 converts the incoming AC signal from the hub 104 into an appropriate DC voltage (e.g., between about 1 V DC and about 5 V DC) for powering the satellite 106. In some implementations, the satellite 106 includes between 1 and 64, between 1 and 32, between 1 and 16, or between 1 and 8 channels that are configurable as recording or stimulation channels.

In some implementations, each of the programmable logic 204, programmable logic 226, and the programmable logic 234 are implemented as special purpose logical circuitry, such as a field programmable gate array (FPGA) or an application specific integrated circuit (ASIC). In some implementations, one or more of the programmable logic circuits are a general purpose computing device. For example, the FPGA can be an ARM Microcontroller with on-chip eSRAM. The FPGA can include more than 80,000 logic elements and internal storage. In some implementations, the FPGA can also monitor environmental sensors, such as humidity and temperature sensors to measure the internal conditions of the hub 104 and satellites 106.

FIG. 3 illustrates a simplified schematic of the system 100 that demonstrates the flow of data through the system 100. In some implementations, the analysis of the signals received by the satellite 106 is segmented between a combination of the satellites 106, the hub 104, the base station 110, and the offline processor 112.

In a first mode, referred to as an autonomous mode, the analysis of signals is shared between the satellites 106 and the hub 104. In the autonomous mode, the hub 104 is not tethered to an external system (e.g., the base station 110 or the offline processor 112), enabling the patient free movement as the hub 104 and the satellites 106 perform closed-loop control. As an overview of the autonomous mode, the satellite 106 records electrical signals from the patient 102. The satellite 106 digitizes the electrical signals and transmits the signals to the hub 104. The electrical signals are received by the signal processing module 206, which performs feature extraction on the signals. The extracted features are passed to the decoding module 208, which determines a neuropsychiatric state of the patient 102. The neuropsychiatric state information is passed to the control module 210, which determines a stimulation paradigm the satellites 106 should apply in stimulating the patient 102.

In more detail of the autonomous mode, the signal processing module 206 receives raw neural signals from the satellites 106 and extracts features that correlate with neuropsychiatric states of interest. Multiple processing algorithms are applied at the hub 104. For example, in some implementations, the signal processing module 206 can perform spike detection and spike sorting. In these implementations, the extracted features are spikes (e.g., action potentials recorded in the raw neural signals). The spikes are extracted from the raw signal and then sorted. Extracting the spike includes saving a portion of raw signal that includes the spike. During the sorting step, the spike is categorized as belonging to one of a plurality of spike templates. Each of the spike templates are associated with different neurons. In other implementations, the signal processing module 206 can perform processing of local field potential (LFP) data (also referred to as "time-frequency analysis") of the raw signal. Prior to performing the analysis, the signal processing module 206 can filter and down sample the raw signal. For example, spikes can have a relatively high frequency component, and signals below about 200 Hz are filtered out of the raw signal. The time-frequency analysis can analyze the lower frequency content of the raw signal, and the signal processing module 206 may filter out the frequency content in the raw signal above about 200 Hz.

In some implementations during the autonomous mode, the hub 104 can conserve power by only analyzing signals from a portion of the satellites 106 or a only a portion of each satellite's channels. The hub 104 can also save power in the autonomous mode by only saving portions of the incoming signals, such as extracted portions containing spikes or not saving any portion of the incoming signals.

During the autonomous mode, to measure spikes, the signal processing module 206 extracts features, such as spikes, by analyzing the incoming signals using algorithms with largely fixed parameter sets. For example, the signal processing module 206 may perform spike sorting by detecting when the signal crosses a set threshold. A portion of the signal, before and after the threshold crossing, is then extracted from the raw signal by the signal processing module 206. The signal processing module 206 classifies (e.g., sorts) the extracted spike as belonging to one of a single unit, multiple unit, or noise template. The spikes are sorted by the signal processing module 206 as belonging to one of the categories based on the similarity of the shape of the extracted spike to the template shape of the spike associated with each of the templates. In some implementations, the extracted spikes are sorted by comparing them with templates stored onboard the hub 104 by computing the Euclidean distances between extracted spike and the templates. Each extracted spike can then be assigned to the template with the shortest Euclidean distance between the template and the extracted spike. In some implementations, during the autonomous mode, the spike templates and threshold are constant and provided to the hub 104 from the base station 110 as configuration settings.

Still referring to FIG. 3 and the autonomous mode, the signal processing module 206 outputs the detected features, such as the sorted spikes or the timing thereof, to the decoding module 208. When the signal processing module 206 performs time-frequency analysis, the signal processing module 206 windows the raw signal into bins and calculates the amplitude and phase information of predetermined frequencies in the windows. The amplitude and phase information is calculated by applying a discrete Fourier transform or wavelet transform to the windowed data. Amplitude and phase information for the bins in each of the windows is transmitted to the decoding module 208 as features.

The decoding module 208 receives the extracted features and estimates neuropsychiatric states, such as impulsivity, avoidance, inhibition, and an epileptic state. The estimation of the neuropsychiatric states is based on an estimation model preloaded into the decoding module 208. In some implementations, the neuropsychiatric state is influenced by the stimulation from the satellites 106. For example, if the neuropsychiatric state is an epileptic state (e.g., a seizure), the stimulation is configured to stop the seizure. In some implementations, the decoding module 208 uses a fixed-gain matrix multiplication or a Bayesian update algorithm to determine the neuropsychiatric state, where the parameters of the algorithms are preconfigured on the hub 104.

The output of the decoding module 208 is supplied to the control module 210. The control module 210 determines, based on the estimated neuropsychiatric state, whether to stimulate the patient's tissue via the satellites 106. The control module 210 can select the amplitude, duration, frequency, pulse width, and selection of channels through which the stimulation is delivered by each of the satellites 106. In some implementations, some or all of the functions of the signal processing module 206, decoding module 208, and control module 210 can be executed by one or more processors within the satellite 106.

Still referring to FIG. 3, in a second mode of operation, termed the "base boost" configuration, the hub 104 offloads a portion of the analysis to the base station 110. As an overview, the base boost configuration mode enables adaptive, closed-loop control. During the base boost mode, the hub 104 transmits recorded signals (or portions thereof) to the base station 110, which performs additional analysis on the signals. In some implementations, the additional analysis can include the analysis of additional channels. For example, during the autonomous mode, the hub 104 and satellites 106 may be capable of analyzing only a portion of each satellite's total number of channels. During the base boost configuration, with the aid of the base station 110, substantially all of the satellite's channels are analyzed. In another example, the additional analysis of the signals can include the use of more complex algorithms as compared to those used by just the hub 104 and satellites 106. In some implementations, the base boost configuration may also provide additional controls and a user interface for interacting with the hub 104 and the satellites 106.

As illustrated in FIG. 3, the template adaptation module 228 communicates with the signal processing module 206. As described above, during the autonomous mode, the parameters of the spike detection algorithm and the templates of the spike sorting algorithm are fixed. The template adaptation module 228 can receive, via the LBW transceiver 224, extracted spikes or raw signals and calculate updated spike templates and detection parameters. For example, the template adaptation module 228 can adapt the threshold at which the signal processing module 206 detects a threshold crossing. In this example, the template adaptation module 228 can analyze the incoming signal for noise or signal drift and alter the threshold responsive to these changes.

In some implementations, the hub 104 may not store the raw signal, only storing, for example, extracted spikes. In this example, the template adaptation module 228 can receive and store raw signals from the hub 104, and then analyze the stored signals for drift or changes to the spike templates. In some implementations, the threshold is set to a predetermined number (e.g., 4) of standard deviations above the noise level of the signal by the template adaptation module 228. As the recording characteristics of the electrodes coupled to the satellites 106 change over time (e.g., as fibrous tissue encapsulates the electrodes), the shape of the extracted spikes can change. The template adaptation module 228 can adapt the spike templates such that the templates evolve with the changing shape of the extracted spikes. Similarly, the decoding adaptation module 230 can update the parameters of the decoding module 208 and the control adaptation module 232 can update the parameters of the control module 210 based on the neural signals received from the hub 104. For example, the control adaptation module 232 may determine that the stimulation is becoming less effective over time as, for example, the electrodes of the satellites 106 are encapsulated by fibrous tissue. In this example, the control adaptation module 232 may change the stimulation parameters of the control module 210 such that the satellites 106 are instructed to stimulate with a greater amplitude electrical stimulus.

In another implementation of the base boost configuration, the base station 110 can couple with the hub 104 via the base station's HBW receiver 222. In this implementation, the increased bandwidth of the HBW transmitter 214 enables the hub 104 to offload raw signals to the base station 110. As described above, in some implementations, the hub 104 does not perform analysis on each of the channels of the satellites 106. In this implementation of the base boost configuration, the template adaptation module 228, the decoding adaptation module 230, and the control adaptation module 232 can perform the analysis described above in relation to the signal processing module 206, decoding module 208, and control module 210 on the additional raw signals that are offloaded from the hub 104. During the base boost configuration, power can be supplied to the hub 104 via the charging system 220 to compensate for the additional power consumption required of the hub 104 to continuously transmit data to the base station 110 via the head mounted interface 108.

Still referring to FIG. 3, in a third mode of operation, termed the "computer controlled" configuration, the offline processor 112 performs relatively high computation intensive analysis of the neural signals. In some implementations, this analysis is not performed in real time, but is performed as "offline" analysis.

In some implementations, in the computer controlled configuration, the system can analyze a greater number of channels, and at a higher sampling rate, than compared to the autonomous and base boost configurations. The computer controlled configuration also enables the hub 104 to stream raw signals to the offline processor 112 for long term storage. In some implementations, after implantation of the hub 104 and satellites 106, the system is set to the computer controlled configuration to calculate the parameters and spike templates discussed above in relation to the autonomous configuration. For example, raw neural signals are transmitted to the offline processor 112 via the HBW transmitter 214 of the hub 104. The signals are saved to a storage element of the offline processor 112 for later analysis. Once the data is collected, spike templates are generated by the template training module 240. For example, using principal component analysis (PCA), the principal components are calculated for each of the spikes the template training module 240 detects in the received signals. The principal components are then computed and clustering algorithms, such as k-means clustering, are used to identify the clusters that correspond to physiological spikes. The shape of the spikes in each cluster can be averaged together to generate a spike template for that cluster. The initial parameters (e.g., threshold value) and spike templates are then transmitted to the hub 104 via the LBW transceiver 224. The parameters for the machine learning algorithms the decoding module 208 uses to predict neuropsychiatric states can be calculated by the neuropsychiatric learning module 238. For example, the patient's neuropsychiatric state can be scored by a healthcare professional and synced to the recorded neural signal. The neuropsychiatric learning module 238 can employ machine learning algorithms to detect patterns in the received neural signals (and the extracted features) that indicate the presence of each of the neuropsychiatric states. The parameters for the models to estimate the neuropsychiatric state can then be transmitted to the hub 104.

The control design module 236 can determine the initial stimulation parameters by entering into an open control configuration. During the open control configuration, the control design module 236 initially presents mild stimulations to the patient via the satellites 106. For example, the mild stimulations have a relatively low amplitude. Over a controlled period of time, the control design module 236 can increase the stimulation parameters until a desired effect is detected in the patient 102. In some implementations, the desired effect is a change in the characteristics of the neural signal recorded by the satellites 106. For example, the neural tissue enters a period of inhibition or excitation following the delivery of the stimulation. Another effect can include the presence of a motor twitch. For example, the stimulation can be increased until it causes the activation of a portion of the motor cortex. Activation of the motor cortex can result in a physical motor twitch by the patient 102 or a tingling sensation felt by the patient 102. In these implementations, once the motor twitch is evoked by the stimulation, the final stimulation parameters delivered to the control module 210 are the highest stimulation parameters that did not evoke the motor twitch.

Figure 4:
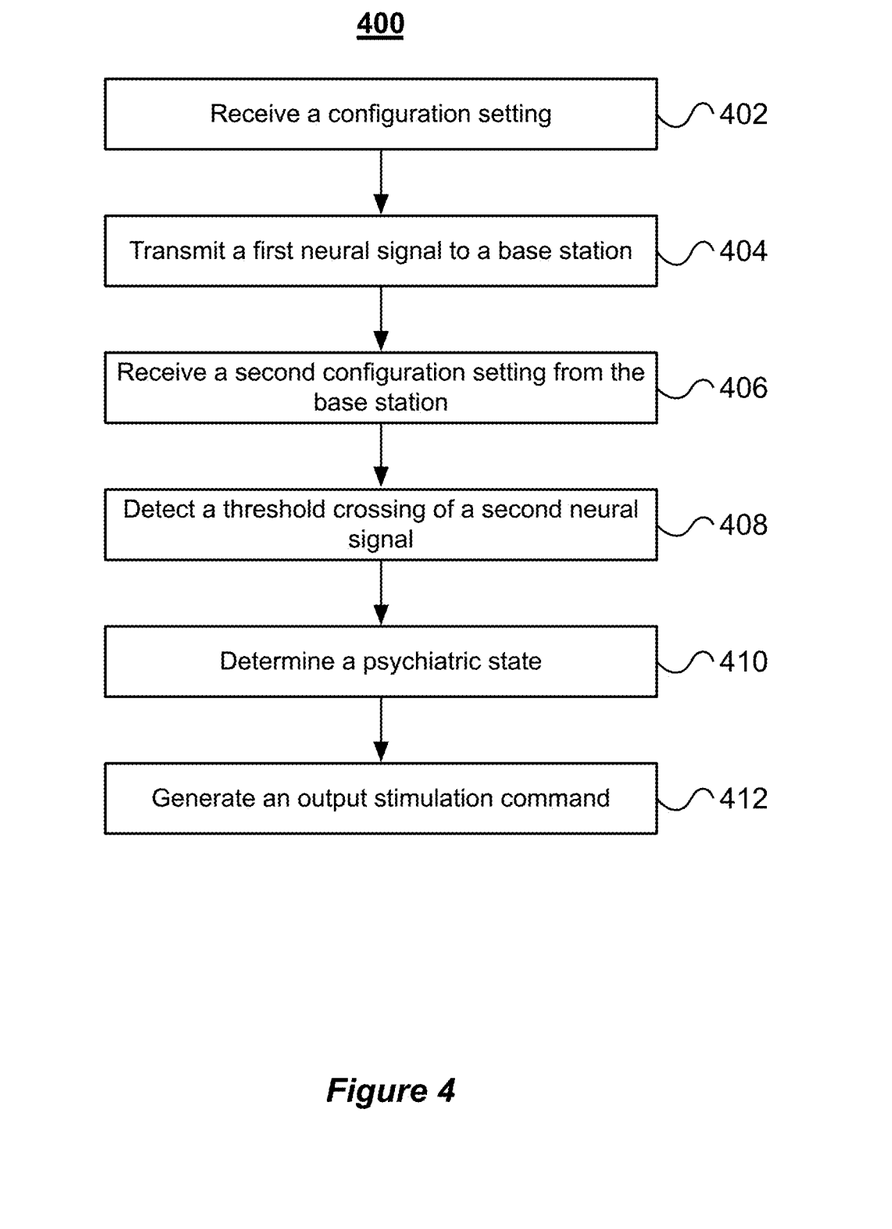
FIG. 4 illustrates a block diagram of an example method for stimulating a patient using the system illustrated in FIG. 1.

FIG. 4 illustrate a block diagram of an example method 400. The method 400 includes receiving configuration settings at a hub (step 402). The method 400 includes transmitting a first neural signal to a base station (step 404). The hub then receives a second configuration settings from the base station (step 406). A threshold crossing of a second neural signal is detected (step 408). The method 400 also includes detecting a neuropsychiatric state (step 410), and then generating an output stimulation command (step 412).

As set forth above and also referring to FIG. 2, the method 400 includes receiving the configuration settings (step 402). The hub 104 receives the configuration settings from the base station 110. The configuration settings are transmitted to the hub 104 via the LBW transceiver 224. The configuration settings can include a plurality of spike templates and a threshold value that the hub 104 and the satellites 106 use for spike detection and spike sorting. The configuration settings can also include parameters for time-frequency analysis algorithms performed by the hub 104 and the satellites 106. The configuration settings also include parameters for the decoding module 208 and the control module 210 that enable the decoding module 208 and the control module 210 to determine a neuropsychiatric state based on the output from the signal processing module 206 and select stimulation parameters, respectively. In some implementations, the configuration settings are generated by the offline processor 112. As described above, after implantation of the hub 104 and satellites 106, raw neural signals are transmitted to the offline processor 112, via the head mounted interface 108. The offline processor 112 analyzes the signals to determine the parameters and spike templates for the configuration settings.

The method 400 also includes transmitting a first neural signal to the base station (step 404). The hub 104 can transmit the first neural signal to the base station 110 via the HBW transmitter 214 or the LBW transceiver 216. In some implementations, a raw neural signal is transmitted to the base station 110 via the HBW transmitter 214. In other implementations, the hub 104 generates a lower bandwidth version of the raw neural signal that the hub 104 transmits to the base station 110 via the LBW transceiver 216. The lower bandwidth signal can include a downsampled version of the raw signal or signal snippets (e.g., spikes extracted from the raw signal). In some implementations, the hub 104 stores the first neural signal locally and transmits the first neural signal to the base station 110 when the base station 110 is in range of one of the hub's HBW transmitter 214 or LBW transceiver 216.

The method 400 includes the hub receiving a second set of configuration settings (step 406). In some implementations, the hub receives the updated configuration settings from the base station via the LBW transceiver. Responsive to the base station receiving the first neural signal, the base station and/or the offline processor analyzes the first neural signal to determine if the configuration settings should be updated. In some implementations, updating the configuration settings can include updating the threshold at which spikes are detected and updating the spike templates. In some implementations, the configuration settings are periodically updated in response to drift in the neural signal and the changing characteristics of the satellites' electrodes. Once the hub receives the updated configuration settings, which can include updated template parameters and an updated threshold value, the signal processing module 206, the decoding module 208, the control module 210, and the satellites 106 are updated with the new configuration settings.

Once the second set of configuration settings is loaded, a threshold crossing is detected (step 408). Referring also to FIG. 3, the hub's signal processing module 206 receives neural signals from the satellites 106. The signal processing module 206 monitors the neural signals for crossings of the threshold. When a threshold crossing is detected, the signal processing module 206 creates a spike snippet by extracting a predetermined amount of the signal before and after the threshold crossing. The signal processing module 206 then performs template matching by matching the extracted spikes to one of the spike templates provided in the updated configuration settings. If the extracted spike is matched with a noise template, the spike is discarded. If the spike is matched with a single or multi-unit template, the timing of the spike is recorded along with an indication of which spike template it matched. The timing and the indication of the matching spike template are transmitted to the decoding module 208 as features. In some implementations, the signal processing module 206 stores the extracted spike for later transmission to the base station 110. In other implementations, the signal processing module 206 performs time-frequency analysis of the neural signal received from the satellites 106. In these implementations, the features sent to the decoding module 208 can include indications of frequency and amplitude within binned windows of the received neural signal.

The decoding module receives the features from the signal processing model and determines a neuropsychiatric state (step 410). In some implementations, the neuropsychiatric state is one of impulsivity, avoidance, inhibition, excitation, and epileptic state. In some implementations, the decoding module uses a fixed-gain matrix multiplication or a Bayesian update algorithm to determine the neuropsychiatric state based on the received features using parameters from the updated configuration settings.

The decoding module transmits an indication of the neuropsychiatric state to the control module, and the control module generates an output stimulation command (step 412). The control module selects stimulation parameters responsive to the type of neuropsychiatric state detected by the decoding module. For example, the control module may select stimulation parameters that cause excitation of neural cells if the cells are determined to be in a state of undesired cellular inhibition. In some implementations, the output stimulation command indicates the amplitude, duration, frequency, pulse width, and selection of stimulation channels or any combination therefore the satellites 106 use when stimulating the patient.

The invention may be embodied in other specific forms without departing from the spirit or essential characteristics thereof. The forgoing implementations are therefore to be considered in all respects illustrative, rather than limiting of the invention.

As utilized herein, the terms "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is therefore to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The indefinite articles "a" and "an," as used herein in the specification and in the claims, unless clearly indicated to the contrary, should be understood to mean "at least one."

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A neural stimulation and recording system comprising:
 a base station comprising:
  a first lower bandwidth transceiver; and
  a higher bandwidth receiver;
 an implantable neural stimulation and recording hub comprising:
  a second lower bandwidth transceiver configured to wirelessly exchange data with the first lower bandwidth transceiver of the base station;
  a higher bandwidth transmitter configured to wirelessly transmit data to the high bandwidth receiver of the base station, wherein
   the higher bandwidth receiver and higher bandwidth transmitter have bandwidths that are higher than the bandwidths of the first and second lower bandwidth transceivers, and the higher bandwidth transmitter has a lower transmission range than the first and second lower bandwidth transceivers; and
  a processor configured to:
   receive, from the base station via the second lower bandwidth transceiver, a first set of configuration settings comprising:
    stimulation parameters for modulating neural stimulation;

recording parameters; and
decode parameters for estimating the state of the patient from recorded neural signals;
transmit a first neural signal to the base station via the higher bandwidth transmitter;
receive, from the base station via the second lower bandwidth transceiver, a second set of configuration settings comprising updated stimulation parameters, updated recording parameters generated responsive to the first neural signal;
reconfigure the stimulation and recording hub based upon the received second set of configuration settings;
determine a patient state responsive to a second neural signal and the updated recording and decode parameters; and
generate an output stimulation command responsive to the determined patient state and updated stimulation parameters.

2. The system of claim 1, wherein the higher bandwidth transmitter comprises a backscatter modulation transmitter.

3. The system of claim 1, wherein the first and second lower bandwidth transceivers are low-energy Bluetooth® transceivers.

4. The system of claim 1, further comprising a processor coupled to the base station.

5. The system of claim 4, wherein the processor generates the configuration setting responsive to an initial neural signal transmitted from the implantable neural stimulation and recording hub.

6. The system of claim 1, further comprising a plurality of satellites coupled to the implantable neural stimulation and recording hub.

7. The system of claim 6, wherein at least one of the plurality of satellites comprises at least one electrode configured to measure the first and second neural signals.

8. The system of claim 7, wherein at least one of the plurality of satellites is configured to deliver an electrical stimulus responsive to the output stimulation command.

9. The system of claim 8, wherein at least one of the satellites includes a cross-point switch such that the at least one electrode that measures the first and second neural signals can be switched to carry the electrical stimulus.

10. A method comprising:
receiving, at an implantable neural stimulation and recording hub from a base station via a lower bandwidth transceiver, a first set of configuration settings comprising neural modulation stimulation parameters, neural signal recording parameters, and decode parameters for estimating the state of the patient from recorded neural signals;
transmitting, from the implantable neural stimulation and recording hub, a first neural signal to the base station via a higher bandwidth transmitter having a higher bandwidth and lower transmission range than the lower bandwidth transceiver;
receiving, at the implantable neural stimulation and recording hub from the base station via the lower bandwidth transceiver, a second set of configuration settings comprising updated neural modulation parameters, updated neural signal recording parameters, and updated decode parameters generated in response to the first neural signal;
reconfigure the implantable neural stimulation hub based on the second set of configuration settings;
determining a patient state responsive to a second neural signal, the updated neural signal recording parameters, and the updated decode parameters; and
generating an output stimulation command responsive to the determined patient state and the updated stimulation parameters.

11. The method of claim 10, wherein transmitting the first neural signal via the higher bandwidth transmitter comprises transmitting the signal using backscatter modulation.

12. The method of claim 11, wherein the higher bandwidth transmitter has a bandwidth between about 5 Mbps and about 50 Mbps.

13. The method of claim 10, wherein the lower bandwidth transceiver is a low-energy Bluetooth® transceiver.

14. The method of claim 10, further comprising transmitting an initial neural signal to an processor coupled to the base station.

15. The method of claim 14, further comprising generating, by the processor, the configuration setting responsive to the initial neural signal.

16. The method of claim 10, further comprising detecting the first neural signal by at least one of a plurality of satellites coupled to the implantable neural stimulation and recording hub.

17. The method of claim 16, further comprising delivering, by at least one of the plurality of satellites, an electrical stimulus responsive to the output stimulation command.

18. The method of claim 17, further comprising switching, using a cross point switch, an electrical connection at least one of the satellites, such that a same electrode at one of the satellites both detects the first neural signal and delivers the electrical stimulus.

\* \* \* \* \*